United States Patent [19]

Auman et al.

[11] 4,208,266
[45] Jun. 17, 1980

[54] EXHAUST GAS OXYGEN SENSOR

[75] Inventors: John T. Auman, Washington; Donald F. Mennucci, Mt. Clemens; James B. Ricketts, Jr., St. Clair Shores, all of Mich.

[73] Assignee: General Motors Corporation, Detroit, Mich.

[21] Appl. No.: 955,158

[22] Filed: Oct. 27, 1978

[51] Int. Cl.² .............................................. G01N 27/58
[52] U.S. Cl. ................................................... 204/195 S
[58] Field of Search ............................... 204/1 S, 195 S

[56] References Cited

U.S. PATENT DOCUMENTS

| Re. 29,209 | 5/1977 | Sayles | 204/195 S |
|---|---|---|---|
| 2,830,945 | 4/1958 | Keidel | 204/195 W |
| 3,546,086 | 12/1970 | Sayles | 204/195 S |
| 3,835,012 | 9/1974 | Hemak | 204/195 S |
| 3,909,385 | 9/1975 | Spielberg et al. | 204/195 S |
| 4,021,326 | 5/1977 | Pollner et al. | 204/195 S |
| 4,038,034 | 7/1977 | Nakajima et al. | 23/255 E |
| 4,057,477 | 11/1977 | Weyl et al. | 204/195 S |
| 4,065,372 | 12/1977 | Hacker et al. | 204/195 S |
| 4,115,235 | 9/1978 | Capone | 204/195 S |
| 4,128,458 | 12/1978 | Obiaya | 204/1 S |

Primary Examiner—G. L. Kaplan
Attorney, Agent, or Firm—Robert J. Wallace

[57] ABSTRACT

A galvanic exhaust gas sensor having a solid electrolyte disc having a porous electrode thereon for detecting oxygen partial pressure in an exhaust gas stream varying in its flow and composition and having a shield protecting the porous electrode from direct impingement of exhaust gas stream. The shield includes means for accelerating exhaust gas from across the disc face at exhaust gas stream velocities and pressures below a preselected level and for maintaining said flow more constant at exhaust gas stream velocities and pressures above the preselected level, effective to more accurately sense variations in oxygen content of the exhaust gas stream at a porous electrode.

3 Claims, 4 Drawing Figures

EXHAUST GAS OXYGEN SENSOR

BACKGROUND OF THE INVENTION

This invention relates to a galvanic sensor of the solid electrolyte type that is responsive to oxygen content in an exhaust gas. It more particularly relates to improvements in exhaust gas flow over a disc of solid electrolyte in an internal combustion engine exhaust gas sensor.

The solid electrolyte in galvanic exhaust gas oxygen responsive sensors must be heated to an elevated temperature for the sensor to be opertive. At higher temperatures, the solid electrolyte exhibits high ionic conductivity. The earlier U.S. Ser. No. 787,900 Howarth, filed Apr. 15, 1977, now U.S. Pat. No. 4,129,099 and entitled "Galvanic Exhaust Gas Sensor," discloses that the sensor can be heated by the exhaust gas or by a resistance type heater. It also cites earlier work in maintaining the electrolyte at a constant operating temperature. Further, it discloses an electrolyte dopant for making the sensor output voltage insensitive to temperature variations above a predetermined temperature.

The sensors referred to above include an oxygen conductive solid electrolyte body, usually of partially or fully stabilized zirconia, having negligible electron conductivity. Thin porous platinum electrodes on opposite faces of the body respectively serve as a reference and exhaust gas electrode. It is customary to prevent direct impingement of the exhaust gases on the zirconia element, so as not to erode the thin platinum electrode. This also slows the exhaust gases down somewhat so that they can be more fully equilibrated at the electrode. A variety of shield configurations and porous electrode coatings have already been proposed to provide improved exhaust gas flow over the exhaust gas electrode.

I have recognized that the exhaust gas stream not only varies in composition but also in its flow. It changes in pressure and velocity, as well as in temperature. These variations may induce changes in sensor output voltage, even though oxygen concentration in the exhaust gas remains substantially constant. Such variations can even completely mask subtle changes in oxygen content of the exhaust gases.

This invention involves a disc-like electrolyte body in a unique housing assembly. The assembly includes a shield over the exhaust gas electrode for stabilizing exhaust gas flow over that electrode. With the more stable exhaust gas flow, the exhaust gas electrode can be more sensitive to variations in oxygen content in the exhaust gas. If flow is stabilized, constant temperature of a heated sensor can be more readily maintained, particularly if the solid electrolyte is isolated from thermal conduction with its housing. In a preferred example, the shield increases exhaust gas flow over the exhaust electrode at low exhaust gas stream flows, and limits flow over that electrode at higher stream flows. With a more stable exhaust gas velocity and pressure at the exhaust electrode, the electrode is more responsive to variations in oxygen content in the exhaust gas. More constant but lower level flows over the electrode may even make the sensor less sensitive to momentary temperature fluctuations in exhaust gas temperature. Preferably, flow through the sensor is generally constant at all exhaust gas stream flows appreciably above the lowest stream flow normally occurring during engine operation, such as at engine idle.

OBJECTS AND SUMMARY OF THE INVENTION

It is an object of this invention to provide a new exhaust gas oxygen responsive sensor construction that provides a more constant flow of exhaust gas over the exhaust electrode at exhaust gas stream flows above predetermined levels.

Another object of the invention is to provide a more constant temperature sensor, even when the sensor does not have a discrete heater.

The invention comprehends a galvanic exhaust gas sensor having a solid electrolyte disc with a porous electrode thereon for exposure to a stream of exhaust gases from an internal combustion engine. As conventional, a shield protects the electrode from direct impingement of the exhaust gas stream. However, the shield also includes means for isolating the porous electrode from variations in exhaust gas stream flow. Exhaust gas flow passages in the shield have a critical, i.e. sonic, flow that is reached significantly below the maximum exhaust gas stream flow. In most instances, the critical flow through the sensor shield is reached by all exhaust gas stream flows appreciably above engine idle conditions. In a preferred form, the means for maintaining constant flow is a cylindrical convergent-divergent channel normal to the face of a solid electrolyte disc. The channel is divided into a plurality of convergent-divergent longitudinal passages by several longitudinal guide vanes, and conductive heat transfer between the electrolyte disc and the sensor housing is minimized.

BRIEF DESCRIPTION OF THE DRAWING

Other objects, features and advantages of the invention will become more apparent from the following description of preferred examples thereof and from the drawing, in which.

DESCRIPTION OF THE PREFERRED EMBODIMENTS

Figure 1:
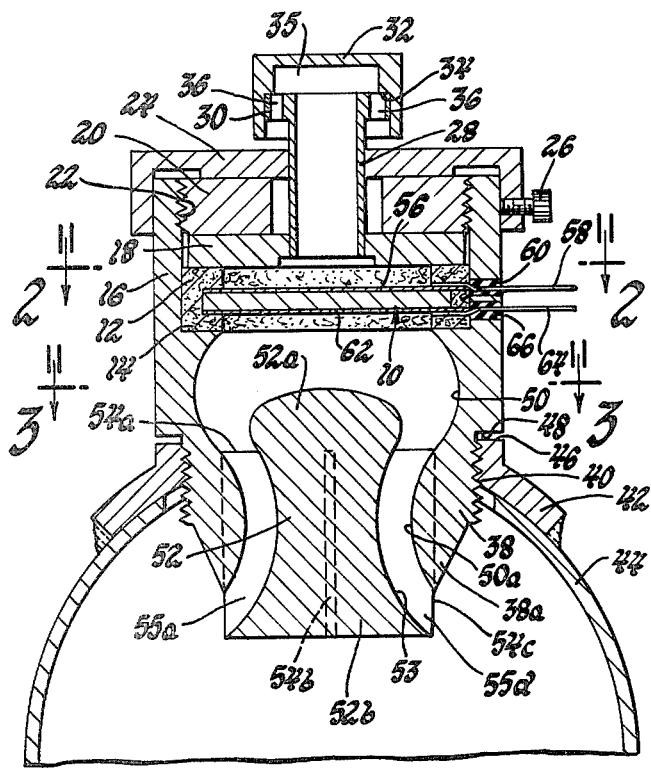
FIG. 1 shows a longitudinal sectional view of the exhaust gas sensor of this invention, as disposed in an engine exhaust conduit.
Figure 2:
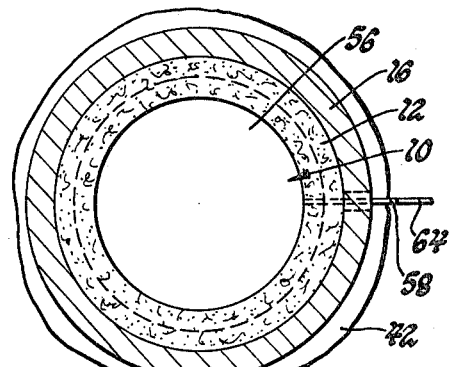
FIG. 2 shows a sectional view along the line 2—2 of FIG. 1.
Figure 3:
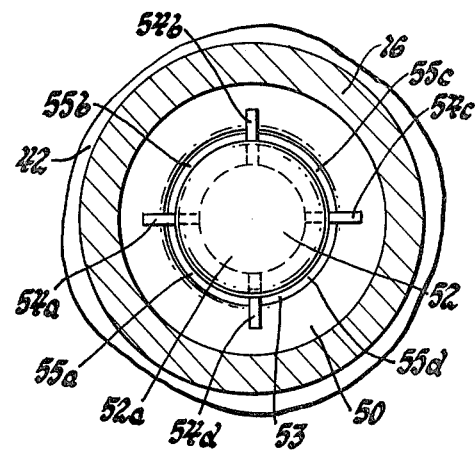
FIG. 3 shows a sectional view along the line 3—3 of FIG. 1.

The exhaust gas sensor of FIGS. 1-3 has a circular solid electrolyte disc 10 of partially or fully stabilized zirconia, thoria or the like. For example, substantially pure zirconia sintered with 4-7 mole percent yttria can be used. Solid electrolyte disc 10 is nested within and peripherally supported by a circumferential annular asbestos gasket 12. Disc 10 is about 2.1 centimeters in diameter. Gasket 12 is inwardly circumferentially flanged above and below disc 10, so that it has a U shape in cross section. If desired, asbestos gasket 12 can be rapidly split transverse to the sensor axis to facilitate assembly with electrolyte disc 10. Asbestos gasket 12 is, in turn, supported on an inner circumferential shoulder 14 about 0.3 centimeter wide within a surrounding hollow cylindrical housing 16. Housing 16 has an outer diameter of about 2.9 centimeters at shoulder 14, and an inner diameter of about 2.4 centimeters immediately above shoulder 14. Gasket 12 minimizes, and for all practical purposes prevents, thermal conduction between disc 10 and housing 16. It also provides an exhaust gas seal along housing shoulder 14. Because disc 10 is thermally isolated from housing 16, disc 10 can be more rapidly heated to operating temperatures when it is cold. Heat applied directly to the disc does not immediately flow by conduction into the housing 16, which can serve as a heat sink. Hence, the housing 16 does not also have to be at the same temperature as disc 10 for the disc 10 to be at an elevated temperature. Contacting the upper surface of asbestos gasket 12 is an annular metal or ceramic retainer 13. Retainer 18 is clamped against asbestos gasket 12 by an externally threaded metal washer 20. Housing 16 is internally threaded at 22 to receive the externally threaded metal washer 20. Over threaded metal washer 20 is a circular housing cover 24, that is retained on housing 16 by a thumb screw 26.

Housing cover 24 has a coaxial air inlet tube 28, the upper end of which has a circumferential outward flange 30. The upper end of air inlet tube 28 is closed by means of a cup-shaped cover 32 having an inner circumferential shoulder 34. Cup shoulder 34 seats on tube flange 30 to space the cup and tube ends apart and form a chamber 35. A plurality of openings 36 through a flange 30 communicate chamber 35 with ambient air.

Inlet tube 28 is coaxial with housing cover 24 which is in turn coaxial with housing 16. It is also coaxial with disc 10, asbestos gasket 12, retainer 18 and threaded metal washer 20. It extends through threaded washer 20 and nests within the inner periphery of annular retainer 18. The upper surface of electrolyte disc 10 is thus exposed to ambient air entering tube flange openings 36. If the spacing between the upper surface of disc 10 and the lower surface of annular retainer 18 is quite close, it might be desirable to appropriately groove (not shown) the lower surface of annular retainer 18, to provide more uniform air distribution across the upper surface of disc 10.

Cylindrical housing 16 has a hollow lower portion 38 of smaller diameter, that is externally threaded at 40. These threads engage internal threads on a circular aperture in an adaptor ring 42 affixed to an exhaust gas stream conduit 44, such as an internal combustion engine exhaust pipe. If desired, a soft metal sealing washer (not shown) can be used between the upper surface 46 of the adaptor ring 42 and external shoulder 48 of housing 16.

Below shoulder 14, the inner wall 50 of housing 16 is also circular. However, it has a diameter that progressively changes with increasing distance away from disc 10 along the housing longitudinal axis. More specifically, with increasing distance away from disc 10, wall 50 diverges from the sensor axis, converges on it, and then diverges again. Wall 50 thus provides a generally bell-shaped cavity in cooperation with disc 10.

A circular member 52 having a similar but smaller bell shape is coaxially disposed within the housing cavity below disc 10. Member 52 is therefore a generally cylindrical member resembling a capstan, and can also be described as a diverter bell. Cylindrical member 52 is closed at its upper end 52a to provide a chamber immediately below disc 10. Cylindrical member 52 has an outer diameter that progressively changes along its length, corresponding to the changing inner diameter of housing 16 below disc 10. It provides an outer wall 53 on member 52 corresponding to the adjacent portions of wall 50. Walls 50 and 53 are uniformly spaced apart to provide an annular channel therebetween. The lower portion 52b of cylindrical member 52 is flared and is axially displaced below the lower end 38a of housing 16. This provides a radially facing open end to the annular channel between member and 52 and walls 50 and 53. The annular channel smoothly intersects with the chamber between disc 10 and the upper end of cylindrical member 52. The annular channel accordingly presents a convergent-divergent annular channel smoothly intersecting with the chamber between disc 10 and the upper end 52a of the cylindrical member 52.

Cylindrical member 52 is supported within the lower end of housing 16 by means of four identical longitudinal members 54a, 54b, 54c and 54d equally spaced about its periphery. Members 54a, 54b, 54c and 54d also divide the annular chamber between walls 50 and 53 into four radially arrayed convergent-divergent longitudinal passages. Since the guide vanes 54a, 54b, 54c and 54d are identical and equally spaced, the longitudinal passages 55a, 55b, 55c and 55d they form are identical too. These four passages provide substantially the same exhaust gas flow across the lower surface of disc 10 regardless as to radial orientation, i.e. theta, of the sensor with respect to the direction of exhaust gas stream flow in conduit 44.

The upper surface of disc 10 has a thin porous platinum electrode 56 thereon connected to an upper terminal lead 58 extending through an electrically insulating ferrule 60 in the side wall of housing 16. Analogously, the lower surface of disc 10 has a thin porous platinum electrode 62 thereon connected to a lower terminal lead 64 extending through an electrically insulating ferrule 66 in the side wall of the housing 16.

The guide vanes 54a, 54b, 54c and 54d provide at least one continuous exhaust gas path in and out of the sensor housing through convergent-divergent passages. At least one passage will always be upstream in conduit 44 and an opposite passage downstream. Along with the scoop effect of the radially oriented lower end of the inlet passage, this results in a pressure drop between oppositely disposed convergent-divergent passages. Critical flow is the same in all passages because the sensor is symmetrical. As previously indicated, critical flow through the passages, particularly the inlet passage if not a symmetrical device, is reached at the lower of exhaust gas stream flow normally occurring in conduit 44. At least three guide vanes should be used, and preferably four, to form at least three, preferably four, identical passages. More guide vanes could be used but the benefits are questionable. Analogously, cylindrical member 52, housing 16 and guide vanes 54a–54d need not be separate elements. Member 16, and the convergent-divergent passages are formed by casting, machining or the like.

To achieve critical flow at about idle conditions in one internal combustion engine exhaust gas system, cylindrical member 52 is approximately 2.1 centimeters long, with a radius of curvature along its length of approximately 1.3 centimeters. The corresponding lower portion of housing 16 has a 1.0 centimeter radius of curvature along the sensor axis and is spaced about 0.3 centimeter away from the member 52. Below shoulder 14, housing 16 is about 2.1 centimeters long. The upper portion of housing interior wall 50 has a radius of curvature along the sensor axis of approximately 0.7 centimeter, a maximum diameter of about 2.2 centimeters at the top 52a of cylindrical member 52, and a minimum in lower portion 50a of about 1.4 centimeters. Disc 10 and top 52a are spaced about 0.6 centimeter apart. The foregoing dimensions are included only by way of example and are not intended to be a limitation. The particular dimensions, spacing, etc., preferred in any application can vary, depending on the sensor size desired. Also, the exhaust gas stream flows encountered will be a factor. However, in any event, the sensor dimensions preferably should be such that critical flow through the convergent-divergent flow passages is obtained from exhaust gas stream flows in conduit 44 occurring when the internal combustion engine is at or near idle. In any event critical, i.e. sonic, flow through the passages is achieved with stream flows in conduit 44 substantially below maximum stream flow therein. Stream flow in conduit 44, of course, is principally determined by stream velocity and pressure. In this embodiment of the invention, constant flow through the sensor is achieved at low stream flows independent of sensor radial orientation in the exhaust gas stream. Hence, the sensor can be simply mounted in conduit 44 merely by threading it into a circular opening, in a conventional manner.

It may be preferred to make cylindrical member 52 hollow (not shown), to reduce its heat sinking effect, and thereby decrease sensor warm-up time for the sensor. As can be seen, the exhaust gases will contact cylindrical member 52 before they contact disc 10. On the other hand, the heat sinking effect may be preferred. It may reduce minor temperature fluctuations in the exhaust gases before they contact electrode 62.

Figure 4:
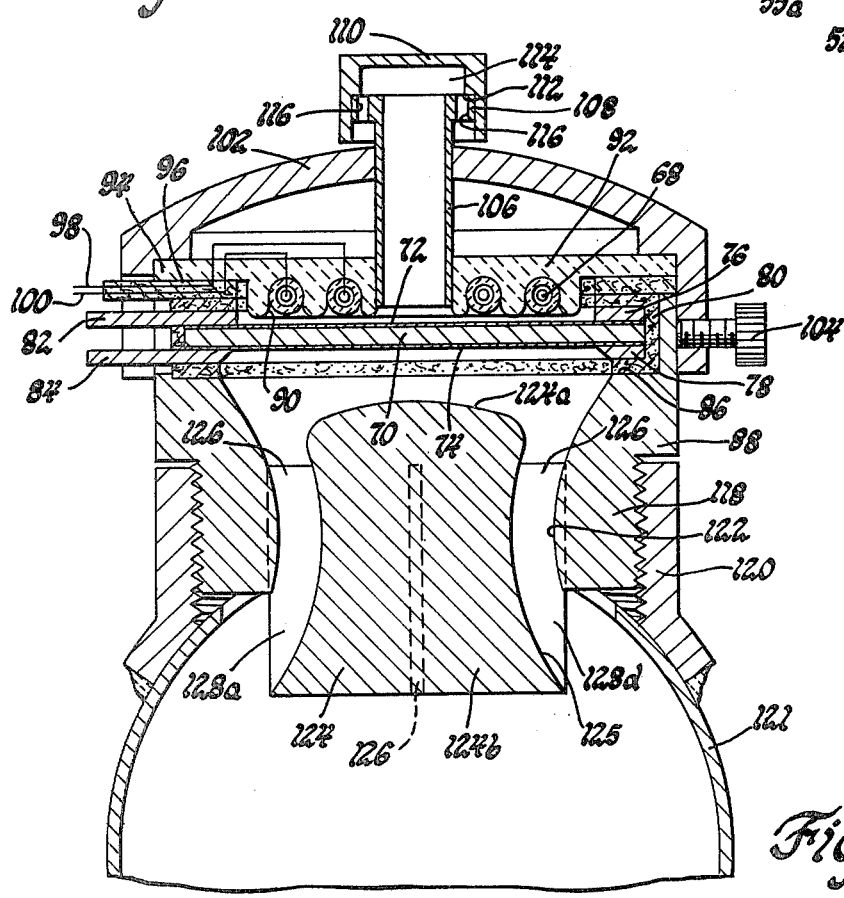
FIG. 4 shows a sectional view of another sensor made in accordance with this invention as disposed in an exhaust gas conduit.

The oxygen sensor shown in FIG. 4 is similar to the embodiment shown in FIGS. 1-3. The FIG. 4 embodiment of this invention is not only intended to operate at a more stable flow and temperature, it is intended to operate at a constant temperature. For this reason a resistance heating element 68 is included in the sensor assembly. More specifically, FIG. 4 includes a circular electrolyte disc 70. Disc 70 has an upper thin porous platinum electrode 72 and a lower thin porous platinum electrode 74. Upper platinum electrode 72 is in contact with an upper coaxial circular metal washer 76. Lower platinum electrode 74 is in contact with a lower coaxial circular metal washer 78. Electrolyte disc 70 and its contact washers 74 and 78 are coaxially nested within a circumferentially surrounding circular asbestos gasket 80. Gasket 80 is inwardly circumferentially flanged above and below washers 76 and 78. The upper contact washer 76 has an outward radial tang 82 extending through asbestos gasket 80 for attachment of an external terminal lead for electrode 72. Analogously, the lower contact washer 78 also has an outward radial terminal lead tang 84 for electrode 74. The disc-washer-gasket assembly is supported on a circumferential inner shoulder 86 of a surrounding cylindrical hollow metal housing 88. Tangs 82 and 84 of the contact washers extend through an opening in the side wall of housing 88, and a corresponding opening in housing cover 102.

Electrolyte disc 70 is heated by means of a resistance heating element 68 that is affixed within a groove 90 on the lower surface of a circular ceramic plate 92. Plate 92 has a circumferential flange 94. Beneath flange 94 is an annular asbestos gasket 96 through which terminal leads 98 and 100 for element 68 extend. The aforementioned elements within housing 88 are clamped against housing inner shoulder 86 by an overlying circular cover 102, which is retained on housing 88 by a thumb screw 104.

Cover 102 has an air inlet tube 106, analogous to the air inlet tube 28 in FIGS. 1-3. Air inlet tube has a circumferential flange 108 at its upper end over which is seated a tube cover 110. Cover 110 has a circumferential inner shoulder 112 which seats on tube flange 108 to provide an associated chamber 114 at the upper end of tube 106. A plurality of apertures 116 in the tube flange 108 permit ambient air to enter the chamber 104, and thus air inlet tube 106. The lower end of air inlet tube 106 extends through a central aperture in the heater ceramic plate 92, whereby upper platinum electrode 72 is placed in communication with the ambient air.

As in the preceding embodiment of this invention, cylindrical housing 88 has an externally threaded smaller diameter lower portion 118 by which the sensor is mounted within an internally threaded adaptor ring 120 on an exhaust conduit 121. A soft metal sealing ring (not shown) can be used between housing 88 and adaptor ring 120, if desired. The lower part of housing 88 has a cylindrical wall 122 that gradually decreases in diameter and then increases, with increasing distance below electrolyte disc 70. Thus, wall 122 progressively converges and then diverges away from the center axis, to provide a generally bell-shaped cavity within housing 88 below disc 70.

A somewhat smaller bell-shaped cylindrical member 124 is coaxially disposed within the housing cavity below the disc 70. Like the foregoing member 52, it also resembles a capstan and can also be referred to as a diverter bell. Slightly below its upper end 124a, cylindrical member 124 has an outer diameter that progressively changes along its length. The changing diameter provides an outer wall 125 on cylindrical member 124 generally parallel the inner wall 122 of housing 88. Walls 122 and 125 are a constant distance apart in their overlapping portions below upper end 124a, to provide an annular channel therebetween, analogous to that shown more fully in FIGS. 1-3. The lower portion 124b of the cylindrical member 124 is axially outwardly displaced from the lower end of housing 88 to provide a radially facing open end to the annular channel. The annular channel smoothly intersects with the chamber formed between disc 70 and the upper end of cylindrical member 124. The annular channel accordingly presents a convergent-divergent annular passage smoothly intersecting the chamber between disc 70 and the upper end of the cylindrical member 124. As in the preceding embodiment of FIGS. 1-3, the lower end of the annular channel in FIG. 4 is open in a plane parallel to the direction of flow of exhaust gases in exhaust conduit 121.

Cylindrical member 124 is supported within the lower end of housing 88 by means of a plurality of identical guide vanes 126, similar to guide vanes 54a, 54b, 54c, and 54d in FIG. 1. The guide vanes produce four identical longitudinal convergent-divergent passages uniformly radially arrayed about the sensor axis. Convergent-divergent passages 128a and 128d are shown. In longitudinal section the inner wall 122 of housing 88 can have a radius of curvature of approximately 2.15 centimeters. The outer surface 125 of cylindrical member 124 has a radius of curvature of about 1.8 centimeters, a length of about 2.5 centimeters, and a spacing from wall 122 of approximately 0.4 centimeter. The upper end of cylindrical member 124 is smoothly rounded, and coaxially spaced approximately 0.4 centimeter below electrolyte disc 70. Disc 70 has a diameter of about 8.8 centimeters.

The convergent-divergent passages 128a and 128d in FIG. 4 have a critical flow preselected to be reached at a level of exhaust gas stream flow that occurs substantially at engine idle conditions. At idle conditions an internal combustion engine is operating at its lowest preferred number of revolutions per minute with no load applied. Further, limiting the flow of gases through the sensor also limits the effect of undesirable temperature fluctuations in the exhaust gas stream. This effect, along with the thermal isolation along the disc edges obtained by gasket 80, permits heating element 68 to maintain electrolyte disc 70 at a more uniform temperature. It is believed the convergent-divergent passages of both embodiments of this invention effectively aspirate exhaust gases into the sensor at exhaust stream flows in conduits 44 and 121 below the preselected values. Hence, if critical flow in the sensor passages is obtained slightly above idle, at lower stream flows, exhaust gas flow through the sensor is accelerated. Thus, flow through the sensor is more constant, temperature of the sensor is more stable, and the heating element 68 more closely maintained at a constant temperature in disc 70.

The embodiments of the invention in which an exclusive property or privilege is claimed are defined as follows:

1. In a galvanic exhaust gas sensor having a circular solid electrolyte disc with a flat face having a porous electrode thereon for exposure to an exhaust gas stream of varying velocities and pressures, a generally cylindrical coaxial housing surrounding said disc and a coaxial shield protecting said electrode from direct impingement of said exhaust gas stream, the improvement wherein said shield includes a chamber contiguous said disc face, a plurality of convergent-divergent passages generally normal to said disc face and generally uniformly arrayed about the shield axis, each of said passages having a substantially identical critical flow level, ends on said passages opposite from said disc face generally disposed outwardly from said axis, ends on said passages adjacent said disc face intersecting said chamber, whereby said disc is substantially isolated from exhaust gas stream variations above a preselected level and said sensor is substantially independent of sensor radial orientation in said exhaust gas stream.

2. In a galvanic exhaust gas sensor having a circular solid electrolyte disc with a porous electrode on a face thereof for exposure to an exhaust gas stream of varying velocities and pressures, a generally cylindrical coaxial housing surrounding said disc and coaxial shield protecting said electrode from direct impingement of said exhaust gas stream, the improvement whereby said shield comprises a tubular extension on said housing, a cylindrical member coaxially disposed within said housing extension and having inner and outer ends, said inner end of said cylindrical member being closed and spaced from said porous electrode to form a chamber therewith, said outer end being flared and axially displaced outward of said extension, respective inner and outer facing surfaces on said tubular extension and cylindrical member being uniformly radially spaced apart and forming a convergent-divergent annular channel extending from said flared end to said chamber, and a plurality of uniformly radially arrayed longitudinal members supporting said cylindrical member within said tubular extension and dividing said channel into a plurality of longitudinal passages, whereby each passage has a similar critical flow, said critical flow is attained at substantially less than maximum exhaust gas stream flow transverse to said shield, and flow through the sensor shield is independent of sensor radial orientation.

3. A galvanic exhaust gas sensor including a circular solid electrolyte disc with a porous electrode on a face thereof for exposure to an exhaust gas stream of varying velocities and pressures, a generally cylindrical coaxial housing surrounding said disc, a heater in said housing for warming said disc, means for preventing conductive heat loss from said disc to said housing, a coaxial tubular extension on said housing substantially normal to said disc face through which exhaust gases contact said face, a cylindrical member coaxially disposed within said extension and having inner and outer ends, the inner end of said cylindrical member being closed and spaced from said porous electrode to form a chamber thereat, the outer end being flared and axially displaced outward from said extension, facing inner and outer surfaces of said extension and cylindrical member being uniformly radially spaced apart and forming a convergent-divergent cylindrical channel extending from said flared end to said chamber, and a plurality of uniformly radially arrayed longitudinal members dividing said channel into a plurality of axial passages and supporting said cylindrical member within said extension, whereby electrolyte disc warm-up time is reduced and a substantially constant disc temperature is maintained after warm-up.

* * * * *